United States Patent [19]

Glassman

[11] Patent Number: 4,725,264
[45] Date of Patent: Feb. 16, 1988

[54] DOUBLE BARRELED BILIARY BALLOON CATHETER

[76] Inventor: Jacob A. Glassman, 1680 Michigan Ave., Miami Beach, Fla. 33139

[21] Appl. No.: 719,219

[22] Filed: Apr. 2, 1985

[51] Int. Cl.[4] ............................................. A61M 25/00
[52] U.S. Cl. ..................................... 604/102; 604/283
[58] Field of Search ............................. 604/96–99, 604/102, 280, 283, 170

[56] References Cited

U.S. PATENT DOCUMENTS

| | | | |
|---|---|---|---|
| 550,238 | 11/1895 | Allen, Jr. | 604/102 |
| 871,474 | 11/1907 | Buckner | 604/102 X |
| 2,688,329 | 9/1954 | Wallace | 604/95 |
| 3,459,175 | 8/1969 | Miller | 604/96 X |
| 3,867,945 | 2/1975 | Long | 604/170 |
| 3,977,408 | 8/1976 | Mackew | 604/102 |
| 4,390,017 | 6/1983 | Harrison et al. | 604/283 X |
| 4,431,426 | 2/1984 | Groshong et al. | 604/283 X |

Primary Examiner—Stephen C. Pellegrino
Attorney, Agent, or Firm—Elmer L. Zwickel

[57] ABSTRACT

A double barreled biliary balloon catheter including a lead-in filiform probe designed to be threaded through an incision in the common bile duct to initially by-pass a gallstone therein and subsequently be connected to the lead or bottom end of a catheter including an inflatable balloon. Means is provided to deliver fluid or air into said balloon for inflating same and means to deliver a Hypaque-like dye or a lubricant or irrigation fluid into the common bile duct and around the gallstone. The catheter is further characterized by having a fine filiform probe removably attached to it's distal end to facilitate manipulation of the biliary catheter within the common bile duct.

4 Claims, 8 Drawing Figures

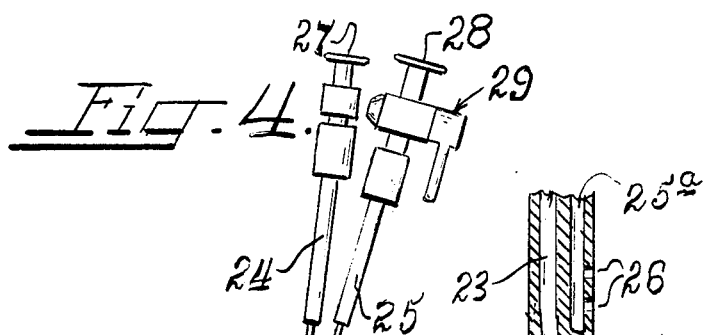
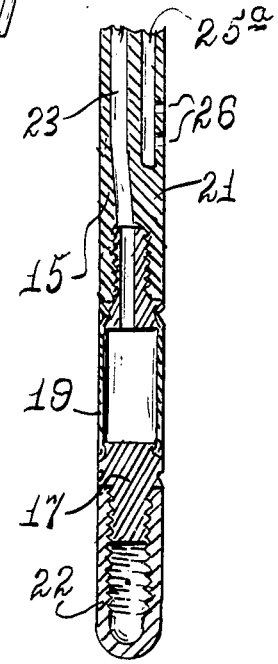
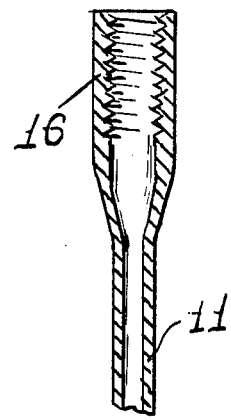
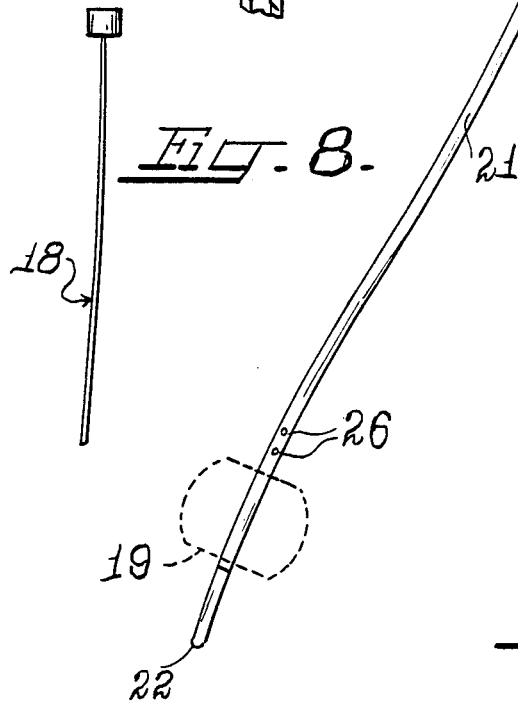
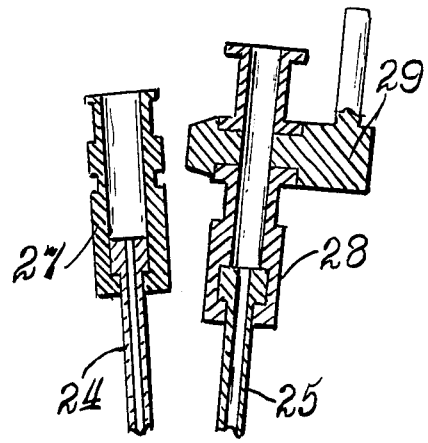

DOUBLE BARRELED BILIARY BALLOON CATHETER

The invention relates to improvements in double-barrel bilariy ballon catheters especially designed for the removal of gallstones from the common bile duct obstruction. More specifically it pertains to an improvement over the well known Fogerty catheter which is primarily distinguishable from the catheter herein disclosed in that the Fogerty catheter is a single barrel catheter mounting a balloon and wherein the catheter has a blunt end, thus lacking any means for the attachment of a fine flexible filiform probe which can be of assistance in by-passing an obstruction in the common bile duct. Otherwise stated, when a gallstone is lodged in the common bile duct it is customary to insert a probe through an incision in the common duct located at a point above the gallstone, and then slowly urge the probe downwardly toward the impacted stone so as to expectantly by-pass the stone and locate it's collapsed balloon beneath the stone. The balloon then is inflated and, if the balloon is properly located beneath the stone, the balloon catheter is carefully withdrawn carrying the stone with it for discharge through the choledochopny incision.

The instant bi-luminal catheter embodies and features a structure not found in the Fogarty catheter, such as by having means on the insert end of the double barrel bilateral catheter that affords quick attachment of the fine filiform probe that can assist the catheter in by-passing the obstruction created by the gallstone. Another feature of the improved structure is the presence of novel means to irrigate and/or lubricate the gallstone and the area surrounding the same or, in select instances, inject a radio-opaque dye to assist in visualization of the stone and balloon on X-ray. For these reasons, the catheter has two passageways, one for the lubricant or dye, and the other for inflating and deflating the balloon. This structure gives the surgeon data as to whether of not there are two or more stones, that it is safe to extract the engaged gallstone by lifting it carefully toward the incise opening.

Another and perhaps a most significant structure for assuring the by-passing of a gallstone by the instrument, is the presence of novel means in the form of a filimorm probe that is attached to the catheter after such probe has successfully by-passed the stone. Otherwise stated, the probe is initially inserted through an incision into the common bile duct and carefully and slowly fed downwardly into same until it either touches or is blocked by the gallstone or passes beyond. Should it be blocked, a second similar filiform probe is inserted and fed toward the gallstone. Should this not pass beyond the stone, a third, fourth, fifth, etc. probe is inserted. As soon as one probe does pass the stone, all remaining probes are then removed and the balloon catheter is screw-threaded onto the exposed end of the remaining filiform probe and further downward movement will carry the catheter balloon into position beneath the stone. As the catheter is moved downwardly, the lead end of the probe passes out of the common duct and moves harmlessly into the duodenum.

Air or fluid then is delivered into one of the catheter barrels to inflate the balloon. The barrel leading to the balloon is shut off to retain the balloon inflated, whereupon the entire assembly is drawn upwardly, carrying the stone with it, until the stone falls out of the incised opening. Should there be additional stones to be removed, the balloon catheter is deflated, the probe is re-inserted and the attached balloon catheter is re-inflated, whereupon the catheter and probe are again withdrawn, carrying the stone with it for extraction.

Accordingly, an object of this invention is to provide an improved form of double-barrelled balloon biliary catheter.

Another object is to provide such a catheter with a balloon adjacent one end which is capable of being selectively inflated when located beneath a gallstone or gallstones to be removed.

Another object of the invention is to provide the end of the catheter having the balloon thereon, with a fitting designed to receive attached thereto a filiform bile duct probe to assist placement of the catheter within the bile duct.

Another object is to provide a double tubular catheter including a normally deflated balloon with novel valve means to effect inflation of the balloon.

Another object is to provide a double barreled balloon catheter with novel means to deliver a dye through one of the catheter barrels into the common bile duct to assist determination of the location of the stone and the balloon, and Another object of the invention is to provide a double barreled balloon catheter with novel means to selectively admit air or liquid into one of the barrels to inflate the balloon and a cut-off valve to keep it inflated.

The structure by means of which the above noted and other advantages of the invention are attained will be described in the following specification, taken in conjunction with the accompanying drawings, showing a preferred illustrative embodiment of the invention, in which:

FIG. 4 is an enlarged detailed view of the double barreled balloon catheter showing the balloon expanded in dotted lines.

FIG. 5 is a detailed longitudinal sectional view of the fittings on the inlet end of the double barreled catheter.

FIG. 6 is a detail sectional view of the lead-in end of the double barreled catheter illustrating the terminus of the barrels and the collapsed balloon and removable cap.

FIG. 7 is a longitudinal sectional view of the terminal end of the filiform probe, and FIG. 8 is a view of a stiffener for the biliary balloon catheter.

DESCRIPTION OF THE INVENTION

Figure 1:
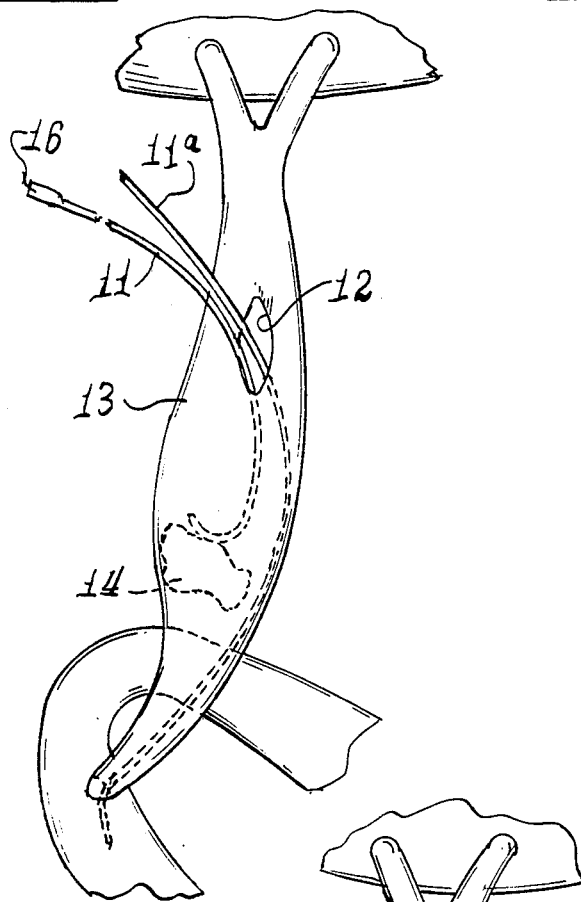
FIG. 1 is an elevational view of a representative common bile duct including an impacted stone, having an incised opening therein through which one or more filiform probes can be inserted.

The present gallstone removing instrument includes a fine flexible filiform probe 11 that initially is inserted into the choledochotomy stoma 12 of the common duct 13 and gently manipulated downwardly until the stone 14 is encoundered. Manipulation of the filiform probe 11 continues in attempting to by-pass the stone. Should this occur the procedure can continue as outlined hereinafter. However, should the filiform probe 11 fail to by-pass the stone, said probe is left in place and a second probe 11a is inserted into the choledochotomy stoma 12 and manipulated in another attempt to by-pass the stone. Should that fail, a third, fourth, etc., probe is inserted and ss soon as one probe 11 does by-pass the stone, the remaining probe are withdrawn from the choledothotomy stoma 12

Figure 2:
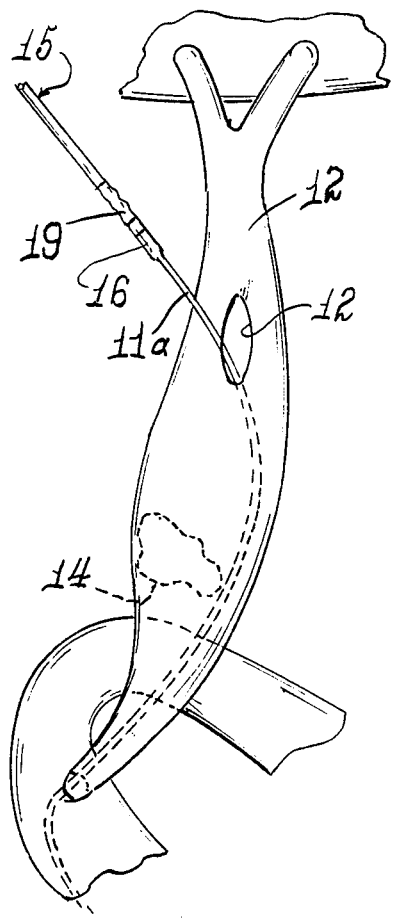
FIG. 2 is a view similar to FIG. 1, wherein there is illustrated a probe that has by-passed the stone and has a double-barreled balloon catheter attached to it's trailing end.
Figure 3:
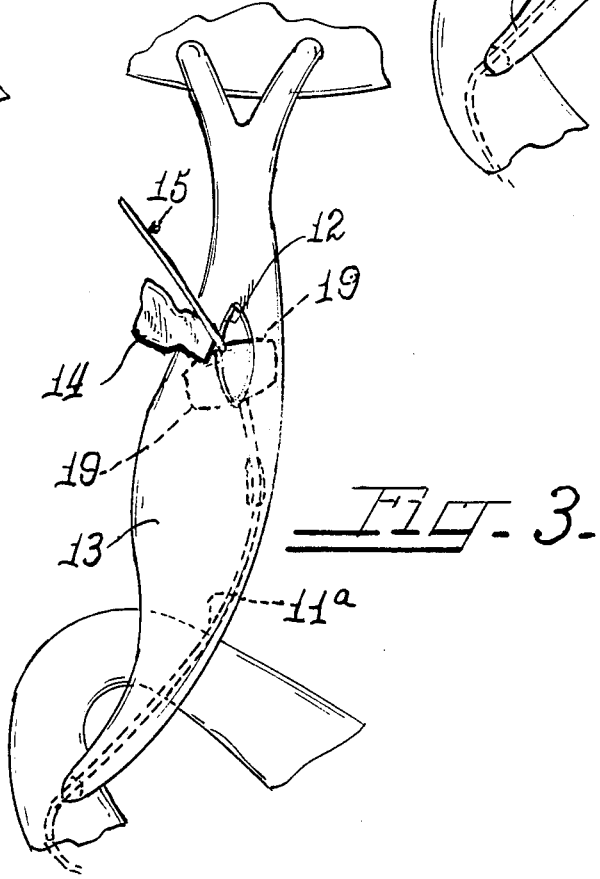
FIG. 3 is another view of the common duct showing the balloon catheter being withdrawn through the incise opening to a point that causes the stone to exit from the common bile duct.

The next step in the procedure for removing the stone 14 involves the attachment of the double barrelled balloon catheter 15 (FIG. 2) on the probe. For this purpose, the probe 11 has a threaded female fitting 16 (FIG. 7) on it's trailing end into which a threaded male fitting 17 (FIG. 6) on the lead end of the balloon catheter is threaded. Specifically, FIG. 7, illustrates a detailed section of the termial end of the filiform lead 11, illustrating the presence thereon of the female fitting 16 which is adapted to be threaded onto the threaded male fitting 17 on the lower extremity of catheter 15, following removal of the cap 22. FIG. 8 is representative of a stiffener probe 18 which may be inserted into the trailing end of catheter 15 to stiffen same should such stiffening be required.

The assemblage 11-15 is then advanced into the common bile duct 13 until the collapsed balloon 19 by-passes the stone 14. At that time the balloon is inflated in a manner to be described hereinafter so as to underlie the stone.

The double barreled balloon catheter 15, best shown in FIGS. 4, 5 and 6, comprises a double barrel tube 21 of requisite length having at it's head end a male fitting 17 normally covered by a round-tip sleeve or cap 22, provided to enhance it's smooth advance into the common bile duct. The balloon 19, shown collapsed in FIG. 6, is located adjacent the fitting 17 and is in flow communication with one barrel passageway 23 in the two barrel tube 21, shown in FIG. 4. The upper or outer end of tube 21 terminates in two separate tube extensions 24–25, one (24) of which is in flow communication through barrel passageway 23 with the balloon 19, and the other (25) is in flow communication through a fluid passageway 25a with a pair of bleed openings 26 adjacent to but not in communication with the balloon 19.

The tube extensions 24-25 are carried on the free end of the tube 21 as shown in FIG. 4. The fitting 27 is intended to receive and regulate the flow of dye and/or a lubricant into barrel 24 for discharge into the bile duct 13 through bleed holes 26. The fitting 28 includes a valve 29 which is opened to admit pressurized air or liquid into the barrel 25 for inflating the balloon 19. To deflate the balloon, the valve 29 is opened to permit the contents of the balloon to escape and the balloon is deflated.

With the inflated balloon 19 lying beneath the stone 14, the balloon catheter 21 is slowly and carefully withdrawn from the common duct through incise opening 12, whereupon the stone 14 is gradually elevated and finally is brought to a position here it fall out of or may be manually removed through the duct opening 12. Should there be an additional stone or stones in the common bile duct the foregoing procedures be repeated after first deflating the balloon.

Although I have described a preferred embodiment of the invention in consideration detail, it will be understood that the description thereof is intended to be illustrative rather than restrictive as many possible details of the structure may be modified or changes without departing from the structure, spirit or scope of the invention. Accordingly, I do not desire to be restricted to the exact construction shown and described.

I claim:

1. A flexible biliary balloon catheter having a lead end and a trailing end, the lead end of said catheter being insertable into the common bile duct for removal of a gallstone from said bile duct, said catheter comprising a flexible tube having first and second passageways therein both open to atmosphere at the trailing end of the tube, a radial bleed-hole in the wall of said tube closely adjacent to it's lead end, one of said passageways communicating with the bleed-hole to deliver fluid into the common bile duct, a fitting secured to the lead end of said catheter, a balloon in said fitting into which the other passageway opens, an exial extension on the lead end of said fitting, and a removable cap normally secured to said extension.

2. A biliary catheter having a lead end and a trailing end, said catheter being insertable into a common bile duct, the catheter comprising a flexible tube having first and second passageways therein both open to atmosphere at the trailing end of the tube, a fitting on the lead end of the catheter including a normally deflated balloon, an externally threaded nipple on the lead end of said fitting, a cap threaded onto the nipple to provide a smooth lead end on the catheter, the first passageway terminating at it's lead end near the fitting, at least one port in the wall of said tube adjacent to said fitting, the said first passageway communicating through said port with the interior of the common bile duct, and the other passageway communicating with the balloon to admit air or fluid thereinto.

3. A flexible biliary balloon catheter having a lead end and a trailing end, said catheter being insertable into a common bile duct for the removal gallstones from said duct, said catheter comprising a flexible tube having first and second tubular passageways therein both opening to atmosphere at the trailing end of the tube, a fitting secured to the lead end of said tube, said fitting being externally threaded at least on one end, a normallly collapsed balloon carried by said fitting, the lead end of said first passageway opening into the balloon, and a filifoam probe attached to said threaded end of said fitting, said filifoam probe being removable to enable the cap to be removably attached to said fitting.

4. A flexible biliary balloon catheter having a lead end and a trailing end, said catheter being insertable into a common bile duct for removal of a gallstone from the common duct, the catheter comprising a flexible tube having first and second passageways therein both open to atmosphere at the trailing end of the tube, the lead end of said first passageway opening into the common bile duct closely adjacent to the lead end of the catheter, a fitting secured to the lead end of said catheter, a balloon carried by said fitting into which said second passageway opens, an axial extension on the lead end of said fitting, and a filiform probe attached to said axial extension, said filiform probe being removable to enable a cap to be attached to said extension.

* * * * *